US012564501B2

(12) United States Patent
Popovic et al.

(10) Patent No.: US 12,564,501 B2
(45) Date of Patent: Mar. 3, 2026

(54) PARTIAL HAND PROSTHESIS

(71) Applicant: Worcester Polytechnic Institute,
Worcester, MA (US)

(72) Inventors: Marko B. Popovic, Somerville, MA
(US); Andrew Strauss, Worcester, MA
(US); Mia Buccowich, Worcester, MA
(US); Brian Fay, Worcester, MA (US)

(73) Assignee: Worcester Polytechnic Institute,
Worcester, MA (US)

( * ) Notice: Subject to any disclaimer, the term of this
patent is extended or adjusted under 35
U.S.C. 154(b) by 522 days.

(21) Appl. No.: 17/696,403

(22) Filed: Mar. 16, 2022

(65) Prior Publication Data

US 2022/0296391 A1     Sep. 22, 2022

Related U.S. Application Data

(60) Provisional application No. 63/161,818, filed on Mar.
16, 2021.

(51) Int. Cl.
A61F 2/58        (2006.01)
A61F 2/70        (2006.01)
(Continued)

(52) U.S. Cl.
CPC ................ A61F 2/586 (2013.01); A61F 2/70
(2013.01); A61F 2/74 (2021.08); G01D 5/145
(2013.01);
(Continued)

(58) Field of Classification Search
CPC ................ A61F 2/586; A61F 2002/587; A61F
2002/7862
See application file for complete search history.

(56) References Cited

U.S. PATENT DOCUMENTS 5,062,855 A  *  11/1991  Rincoe ................ B25J 15/0009
                                                       623/64
7,867,287 B2 *   1/2011  Puchhammer .......... A61F 2/583
                                                       623/64

(Continued)

FOREIGN PATENT DOCUMENTS

KR        1020200050571 A      5/2020
WO          2020251344 A1     12/2020

OTHER PUBLICATIONS

International Search Report, PCT/US2022/020552, Jun. 30, 2022,
pp. 1-4.

(Continued)

*Primary Examiner* — Bruce E Snow
(74) *Attorney, Agent, or Firm* — Armis IP Law, LLC

(57)          ABSTRACT

A prosthetic device and approach for amputee remediation
addresses partial or complete replacement of digits, and
leverages the use of the remaining functional digits for
directing operation of the prosthetic digits. A complete
prosthetic digit replaces an amputated digit from actuated
movement driven by an adjacent functional digit. A partial
amputation leverages residual movement from the remain-
ing digit portion as input to an actuator for amplifying the
intent of the input through a motorized actuator to impart
movement to the prosthetic digit. A wrist harness supports
the apparatus of partial and complete prosthetic digits as a
single appliance. A variable compression feature augments
tension on the wrist harness to tightly engage the prosthetic
appliance to the wrist to offset a gripping load on the
prosthetic digits.

8 Claims, 15 Drawing Sheets

(51) Int. Cl.

| | |
|---|---|
| *A61F 2/74* | (2006.01) |
| *G01D 5/14* | (2006.01) |
| *G16H 40/63* | (2018.01) |
| *A61F 2/76* | (2006.01) |
| *A61F 2/78* | (2006.01) |

(52) U.S. Cl.

CPC ........ *G16H 40/63* (2018.01); *A61F 2002/587* (2013.01); *A61F 2002/7635* (2013.01); *A61F 2002/7862* (2013.01)

(56) References Cited

U.S. PATENT DOCUMENTS

| | | | |
|---|---|---|---|
| 12,011,376 B2 * | 6/2024 | Pulver | A61F 2/80 |
| 2016/0296345 A1 * | 10/2016 | Deshpande | A61F 2/586 |
| 2016/0354215 A1 | 12/2016 | Thompson et al. | |
| 2020/0330246 A1 | 10/2020 | Tognetti et al. | |

OTHER PUBLICATIONS

Ryu, et al., "Development of a lightweight prosthetic hand for patients with amputated finger" Applied sciences, May 20, 2020, vol. 10, Article No. 3536, pp. 1-14.

* cited by examiner

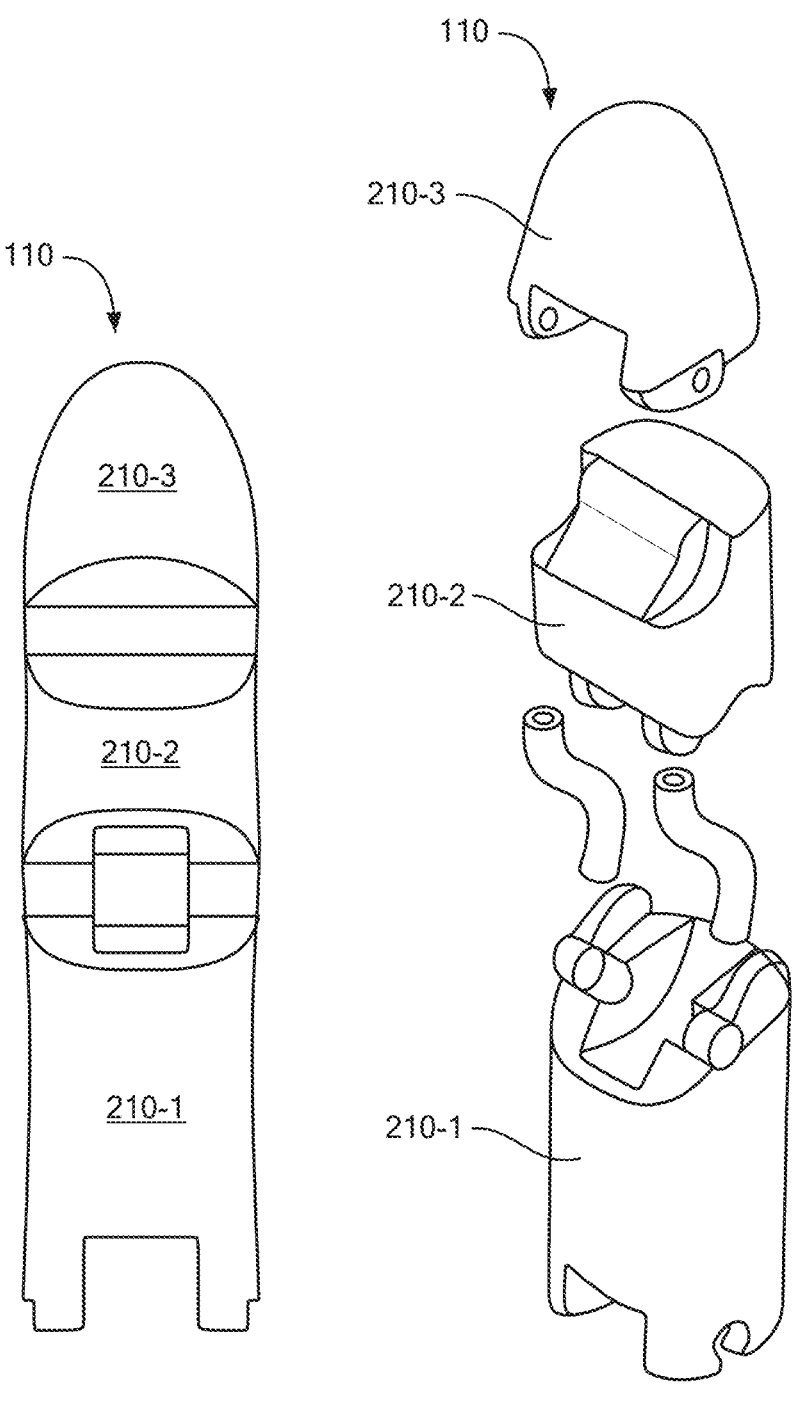
*FIG. 5B*          *FIG. 5C*

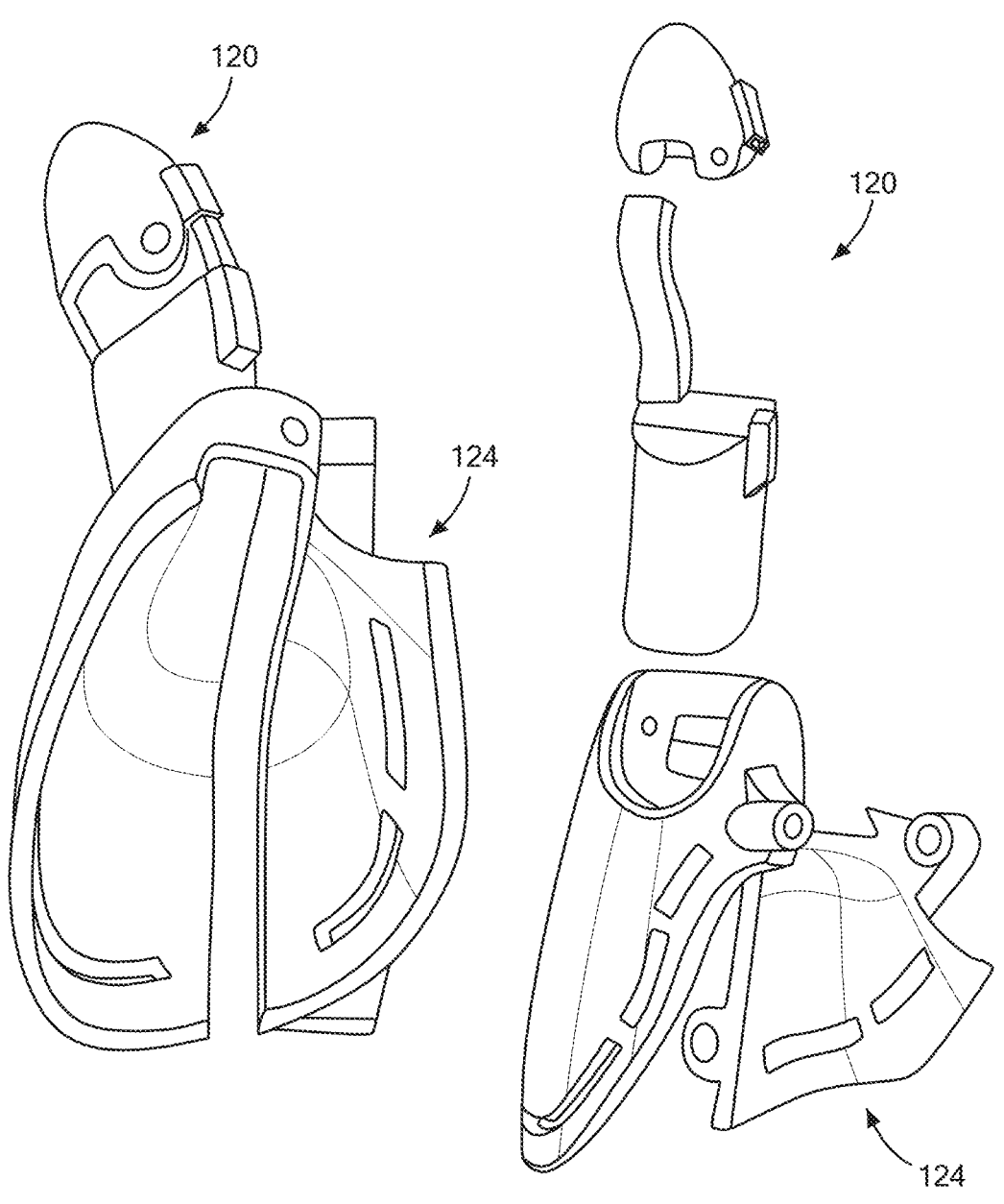
*FIG. 7A*            *FIG. 7B*

PARTIAL HAND PROSTHESIS

RELATED APPLICATIONS

This patent application claims the benefit under 35 U.S.C. § 119(e) of U.S. Provisional Patent App. No. 63/161,818, filed Mar. 16, 2021, entitled "OPTICAL FIBER STRAIN SENSOR," incorporated herein by reference in entirety.

BACKGROUND

Prosthetics attempt to replace a limb or appendage list to trauma or disease. Ideally, a prosthetic can restore some degree of ambulatory or dexterous capability. The most common upper limb amputation in the U.S. is partial hand amputation with a loss of one or more fingers accounting for about 61,000 amputations each year. Prosthetics vary based on the degree of manual control that they return to the user. Some prosthetics are only cosmetic, and passively attach in place of the amputated appendage. In the case of amputation in the close vicinity of the Metacarpophalangeal joint, prosthetic options have little motor movement to expand on.

SUMMARY

A prosthetic device and approach for amputee remediation addresses partial or complete replacement of digits, and leverages the use of the remaining functional digits for directing operation of the prosthetic digits. A complete prosthetic digit replaces an amputated digit from actuated movement driven by an adjacent functional digit. A partial amputation leverages residual movement from the remaining digit portion as input to an actuator for amplifying the intent of the input through a motorized actuator to impart movement to the prosthetic digit. A wrist harness supports the apparatus of partial and complete prosthetic digits as a single appliance. A variable compression feature augments tension on the wrist harness to tightly engage the prosthetic appliance to the wrist to offset a gripping load on the prosthetic digits.

Configurations herein are based, in part, on the observation that prosthetics are often employed to simulate at least the appearance of an extremity lost to injury or illness. Unfortunately, conventional approaches to amputee treatment suffers from the shortcoming that little, if any, function of movement is provided by conventional prosthetic limbs. Prosthetic replacements often require a length of a natural limb and functional joint to impart any movement to the prosthetic replacement. Accordingly, configurations herein provide a system, method and apparatus for addressing partial or complete loss of a digit, and providing a prosthetic with functional, voluntary movement in response to natural motor functions.

In the case of partial hand amputations, there are limited functional options from conventional approaches. Conventional vendors offer options for amputees who still have their proximal or middle phalangeal bones, meaning one or two joints, however for amputations at the metacarpophalangeal (MCP) joint, there is a need for a commercial solution. This is primarily because the majority of partial hand prostheses utilize the movement of these two bones (proximal or middle phalanx) to give the user length and actuation. With these bones removed there is no simple pivot point for the device, making the mechanics of actuation much more complicated.

A prosthetic apparatus as defined herein provides prosthesis support for a multiple digit amputee by determining, for each of a plurality of compromised digits, a degree of residual motor control of a digit position. In the case of a complete amputation, where residual motor control is nonexistent or incapable of mechanical activation, a full digit prosthesis is attached, where the full digit prostheses is responsive to a proximate functional digit for actuated control via a tethered attachment. This approach borrows tethered and/or mechanical movement from a proximate or adjacent digit for operating the prosthetic replacement of the full digit.

If residual motor control is available from a remaining digit portion to manipulate an input device, a prosthetic digit extends from a residual digit portion and connects to a mechanical actuator. The mechanical actuator is responsive to the input device for movement of the prosthesis. A partial digit including a joint and some skeletal portion is engaged to receive user intent via the input device. The mechanical actuator, such as a motor driven pulley, drives articulation of the prosthetic digit attached to the residual natural portion.

In an example configuration, a particular advantage is provided by implementing a "pinching" capability between the thumb and index finger. Evolution has benefited humans from a functional thumb that allows grasping when used in conjunction with other digits, most notable the index finger. Loss of a thumb is therefore a more debilitating injury than amputation of other digits. A particular use case below depicts a scenario where a partial thumb amputation and complete index finger amputation is addressed by a prosthetic device that restores a "grip" between prosthetic thumb and index finger by allowing them to converge together.

An integrated harness aggregates a multiple digit prosthesis for full hand function from a wrist mounted apparatus. The harness engages the full digit prosthesis for replacing an index finger which is actuated by an adjacent middle finger. A receptacle engages a prosthetic digit on a residual thumb portion, and provides simultaneously actuation from a mechanical actuator and a tethered attachment for simulating a pinching movement between a thumb and index finger.

In further detail, the wrist mounted harness defines a hand prosthetic apparatus including a first prosthetic member adapted to engage a digit void resulting from a complete amputation, and a second prosthetic member adapted to engage a partially amputated digit portion. An actuator engages with each respective first and second prosthetic members, where each actuator includes either:

a) a tethered attachment to an adjacent functional digit, such that the prosthetic digit is responsive to a tethered attachment for movement of the respective prosthetic member, or b) a sensor responsive to movement of the digit portion, where the sensor connects to a powered actuator for moving the respective prosthetic member.

The example approach depicts a motorized actuator for the thumb and an adjacency actuator for the index finger, based on a mechanical attachment to the middle finger. Other configurations may encompass different finger/digit arrangements based on the partial/complete amputation state of respective digits.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIGS. 5A-5C show views of a full digit prosthetic in the prosthetic apparatus of FIGS. 1, 3A and 3B;

FIGS. 7A-7B show views of a partial digit prosthetic apparatus of FIGS. 1, 3A and 3B;

DETAILED DESCRIPTION

The description below presents an example of a hand prosthetic apparatus employing a partial digit prosthesis and complete digit prosthesis for imparting a gripping capability with a variable tensioning of wrist engagement for supporting increasing loads from the gripped article.

Configurations below address amputations at the metacarpophalangeal (MCP) joint, for which there are no conventional commercial solutions. This is primarily because the majority of partial hand prostheses require the movement of two remaining bones (proximal or middle phalanx) to give the user length and actuation. With these bones removed there is no simple pivot point for the device, making the mechanics of actuation much more complicated. Patients with full digit amputations are therefore left with cosmetic and aesthetic choices from among conventional prosthetic digits.

Figure 1:
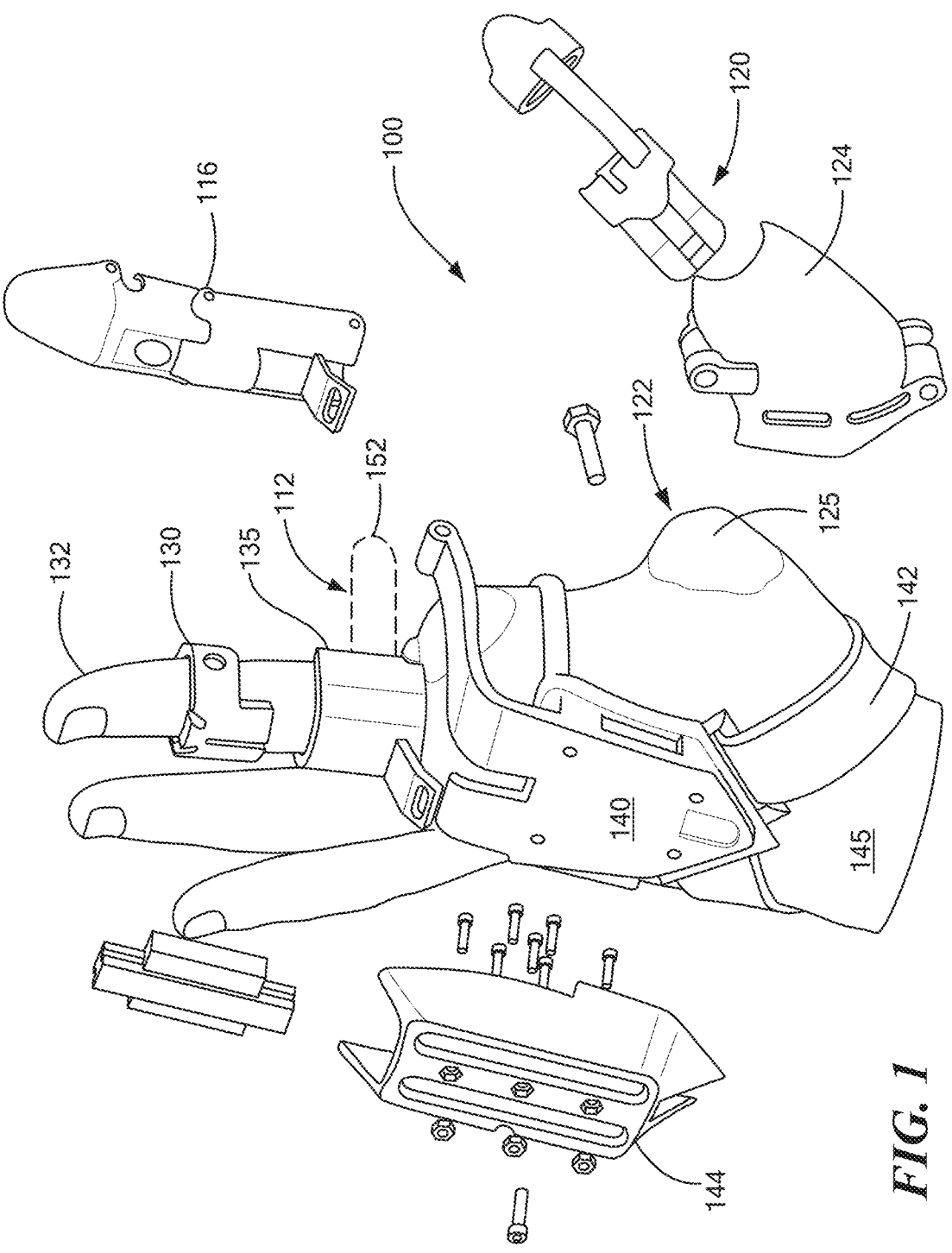
FIG. 1 shows an exploded view of a prosthetic apparatus according to configurations herein.

FIG. 1 shows an exploded view of a prosthetic apparatus according to configurations herein. Referring to FIG. 1, a prosthetic device 100 includes a prosthetic member 110 adapted to engage a digit void 112 of resulting from a complete amputation, and a prosthetic member 120 adapted to engage a partially amputated digit portion 122. An actuator engages with each respective prosthetic member 110, 120. The full prosthetic member 110 includes a tethered attachment 130 to an adjacent functional digit 132, where the prosthetic digit is responsive to the tethered attachment for movement of the respective prosthetic member. A second degree of freedom is provided by a levered or mechanical connection 135, which transfers motion force from an articulated segment through a rigid extension 152.

For the partially remaining digit 122, a receptacle 124 includes a sensor responsive to movement of the digit portion 125. The sensor connects to a powered actuator for moving the respective prosthetic member. The actuator is installed in or attached to a housing 140 of a wrist harness 142 (harness), which wraps around and secures the housing 140 to the wrist 145 of the patient/wearer. A cover 144 secures the housing 140 and harness 142 in place. The full prosthetic apparatus 100 provides, for a complete digit amputee, a prosthetic device operable independent of a preexisting metacarpal portion via a prosthetic member 110 adapted for engaging the wrist 145 at an amputated digit void 112, where the prosthetic member 110 is responsive to movement of the function digit 132 via shared tethered and/or mechanical movement for providing at least two degrees of freedom.

Figure 2:
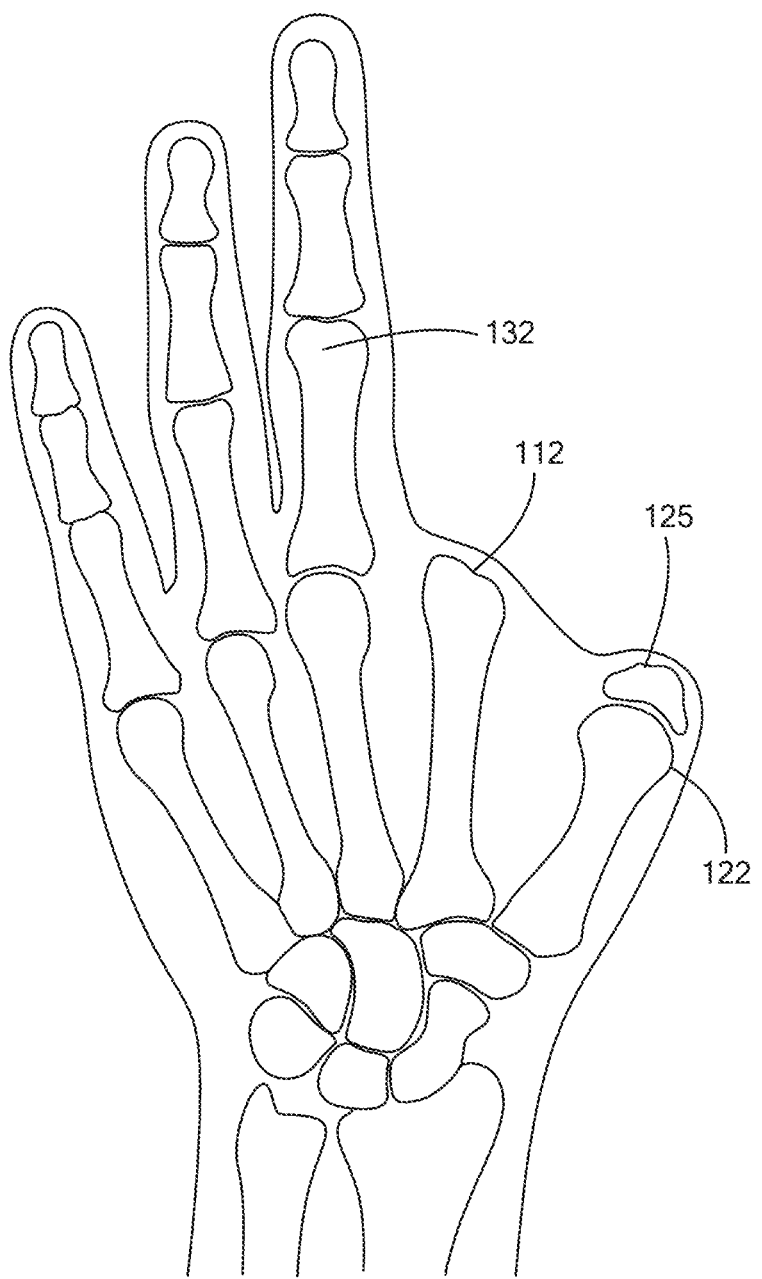
FIG. 2 shows a skeletal view of an amputee suitable for use with the prosthetic apparatus of FIG. 1.

FIG. 2 shows a skeletal view of an amputee suitable for use with the prosthetic apparatus of FIG. 1. In FIG. 2, a full amputation results in an effective void 112 where no jointed or articulated skeletal members remain. A partial amputation leaves a jointed digit portion 125 at the end of the remaining digit 122, which has a fraction of movement of the former digit. This residual movement may be invoked for powered actuation, discussed further below.

Figure 3A:
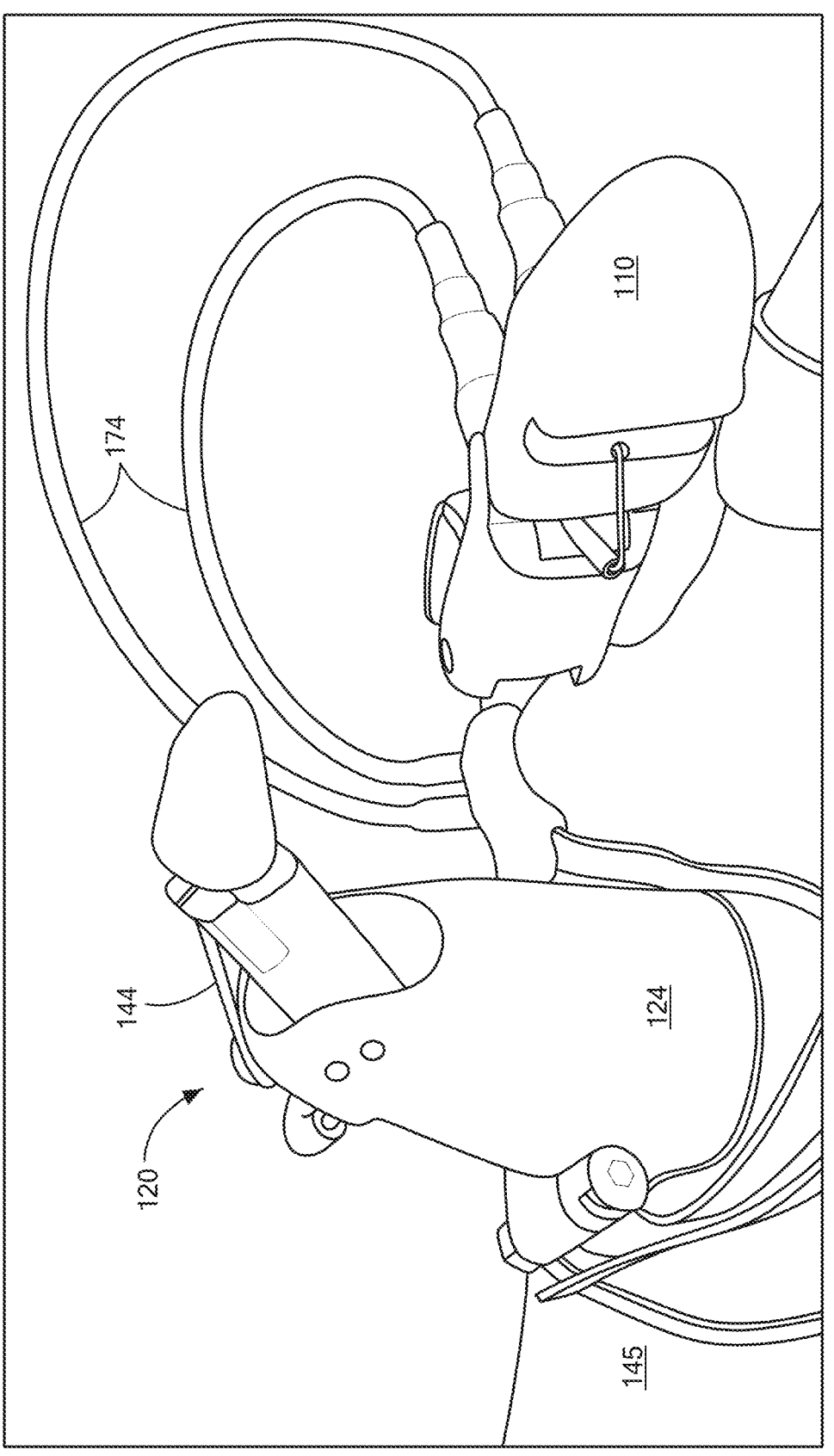
FIGS. 3A and 3B show respective front and side views of the prosthetic of FIG. 1.
Figure 3B:
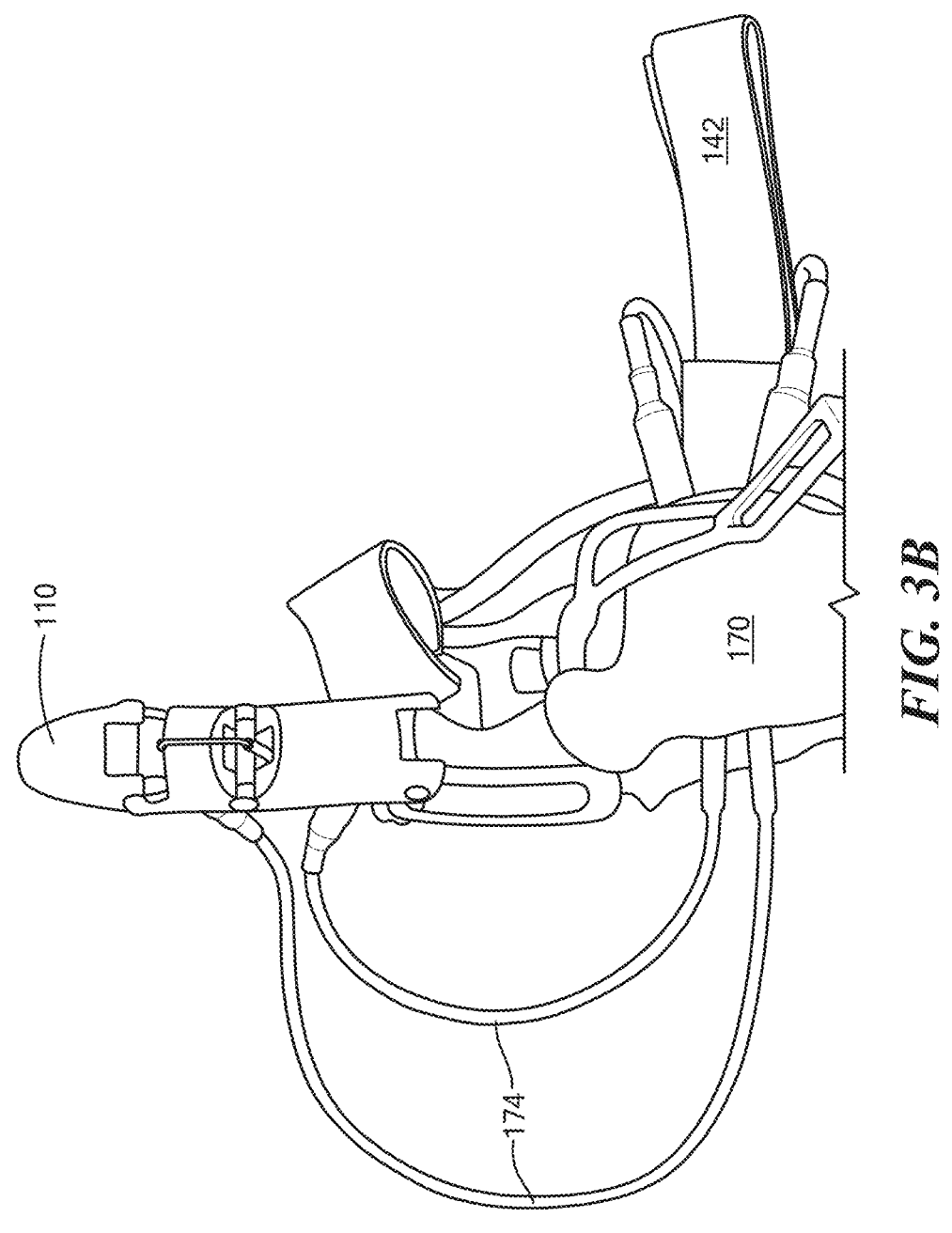

FIGS. 3A and 3B show respective front and side views of the prosthetic of FIG. 1. Referring to FIGS. 1, 3A and 3B, a motor driven pulley is operable to retract a tether 144 attached to the prosthetic member 120 in response to thumb actuation from the digit portion 125 moving within the receptacle 124. The actuator further includes a locking solenoid, discussed further below with respect to FIG. 4. This avoids rollback or unwinding of the tether when a gripped load imposes additional force.

Figure 4:
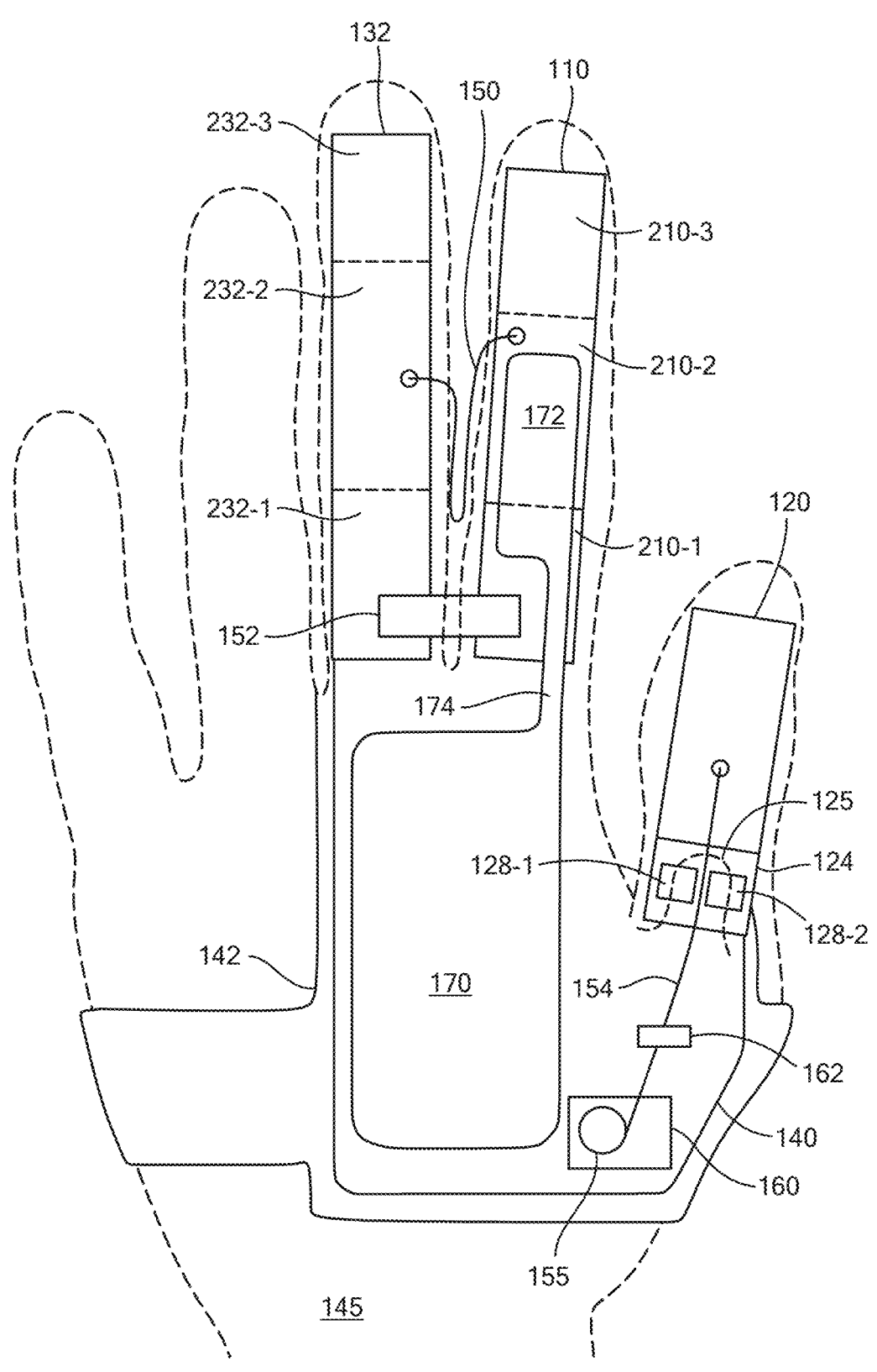
FIG. 4 shows a schematic of the prosthetic of FIGS. 1 and 3A-3B.

FIG. 4 shows a schematic of the prosthetic of FIGS. 1 and 3A-3B. Referring to FIGS. 1-4, the shared movement between the functional index finger 132 and full prosthetic member 110 can be achieved in several ways. Conventional prosthetics offer limited, if any, movement, often only a single range or member with ability to move. The disclosed approach provides multiple degrees of freedom (DOF) of the prosthetic member 110. Each natural digit has several articulated segments, referred to phalanges. The prosthetic member 110 mimics these articulated phalanges 232-1 . . . 232-3 (232 generally) with articulated segments 210-1 . . . 210-3 (210 generally). A flexible cable 150 runs between the prosthetic member 110 and the functional digit 132, where the flexible cable 150 is operable for tensioned actuation of the prosthetic member 110.

A second degree of freedom is provided by an extension member 152. The extension member 152 is firmly attached to and extends from the functional digit 132, and engages the prosthetic member 110 for transference of motion. In other words, the functional digit 132 pushes the prosthetic member 110 from a load bearing rigid attachment.

The combination of tethered actuation and transferred movement articulates different but corresponding articulated segments. Direct motion is most effectively transferred nearest to the metacarpal, or the first articulation from the wrist. Accordingly, the functional phalange 232-1 engages prosthetic segment 110-1 via extension member 152. Phalange 232-2 tethers to prosthetic segment 210-2 via tether 150.

In either case, an elastic return may be engaged with the prosthetic member 110, where the elastic return is configured for complementary movement to the tensioned actuation for opposite movement of the prosthetic member. Restating, once tensioned or transferred movement pushes or disposes the prosthetic member 110, an elastic return pulls it back.

Another approach is to provide a pair of flexible cables between the prosthetic member 110 and the functional digit 132, such that each cable of the pair of flexible cables is configured for tensioned actuation in a direction opposed to an actuated direction of the other flexible cable. In other words, the cables alternate a push-pull arrangement where one cable provides tension at a time.

A further option is to employ a so-called Bowden cable for bidirectional control of a single cable. In this configuration, a noncompressible cable 150 runs between the prosthetic member 110 and the functional digit 132, such that the noncompressible cable is operable for both tension and compression. A sheath encases the noncompressible cable, where the sheath is in slidable communication with the noncompressible cable for bidirectional movement.

A further variation is to employ cables 150-N for multiple segments. In such a configuration, a plurality of articulated segments 210 define the full digit prosthesis, and a respective tethered attachment runs between each of the plurality of articulated segments 210 to a corresponding articulated portion (phalange) 232 of the proximate or adjacent functional digit. In such an arrangement, the plurality of tethered attachments provide multiple degrees of freedom of the full digit prosthesis. As a practical matter, the number of tethers 150-N may approach a practicality limit, as with dual cables between each segment, and multiple tethered segments, as many as 4 or 6 cables may be employed to articulate 2 or 3 phalangeal segments. It should also be noted that complementary movement imposes that a tensioned tether run to an opposed side of the activated articulated segment 210. In other words, when functional digit 132 is articulated ("bent"), a tether would run from the dorsal side of the functional digit 132 to the palmer side of the prosthetic segment 210 to "pull" for corresponding movement.

Adjacent to the full prosthetic member 110 is the partial prosthetic member 120 for the thumb, attached to the wrist harness 142 and housing 140, or base. The wrist harness 142 engages the wrist 145, such that the remaining metacarpal digit portion 122 extends from the wrist harness 142. A receptacle 124 receives the metacarpal portion 125.

For a partial amputation of a digit, the prosthetic member 120 is adapted to engage the post amputation metacarpal portion 125 having residual movement. The prosthetic member 120 defines a receptacle 124 adapted to engage the metacarpal portion 125. One or more sensors 128-1 . . . 128-2 (128 generally) on the base are responsive to movement of the metacarpal portion 125. An actuator 160 is responsive to the sensor(s) 128 for disposing the prosthetic member 120 responsive to the sensor via a motorized tether 154 and corresponding pulley 155. A locking solenoid 162 is responsive to stoppage of the motor driven pulley 155 for maintaining a position of the tether and attached prosthetic member under a load, as when gripping an object.

The harness 142 engages the wrist via one or more flexible straps and/or flexible textile members. Balancing user comfort and functionality are accommodated by a variable tensioning of the harness 142 in response to a load on the prosthetic members 110, 120 indicating a need for more secure engagement with the wrist 145. Accordingly, the harness 142 and housing 140 also supports a fluid receptacle 170 disposed between the harness 142 and the wrist 145, where the fluid receptacle 170 is part of a fluid bladder extending to at least one of the prosthetic member 110, 120 and is responsive to compression of the prosthetic member for forcing fluid between the wrist and the flexible harness substrate to more securely tighten the engagement with the wrist.

In an example configuration, the passively reactive bladder 172 expands when the index finger 110 is under load, thus increasing the compression on the user. The repository 170 in the harness is connected to one or two bladders in the MCP and PIP (Proximal interphalangeal) of the index finger.

When the index finger faces resistance, the water is pushed from the bladder 172 into the harness repository 170, causing it to grasp more tightly to the patient's hand.

The variable tensioning feature invokes the fluid receptacle 170 attached to the wrist harness 142, where the wrist harness supports one or more prosthetic members 110, 120 in communication with the wrist and amputated digits or voids. The bladder 172 extends along the prosthetic member 110 and couples to the fluid receptacle 170 for forming a closed fluid volume via tube 174. The bladder 172 is formed from a flexible material and is disposed to compress based on a gripping force exerted by the prosthetic member 110. Compression forces fluid into the fluid receptacle 170 for compressing the wrist harness 142 against the fluid receptacle 170, causing additional restraint between the wrist, the harness and the load (weight) imposed by the prosthetic member 110, 120. This is particularly useful in a gripping operation formed by disposing both prosthetic members 110, 120 together.

Figure 5A:
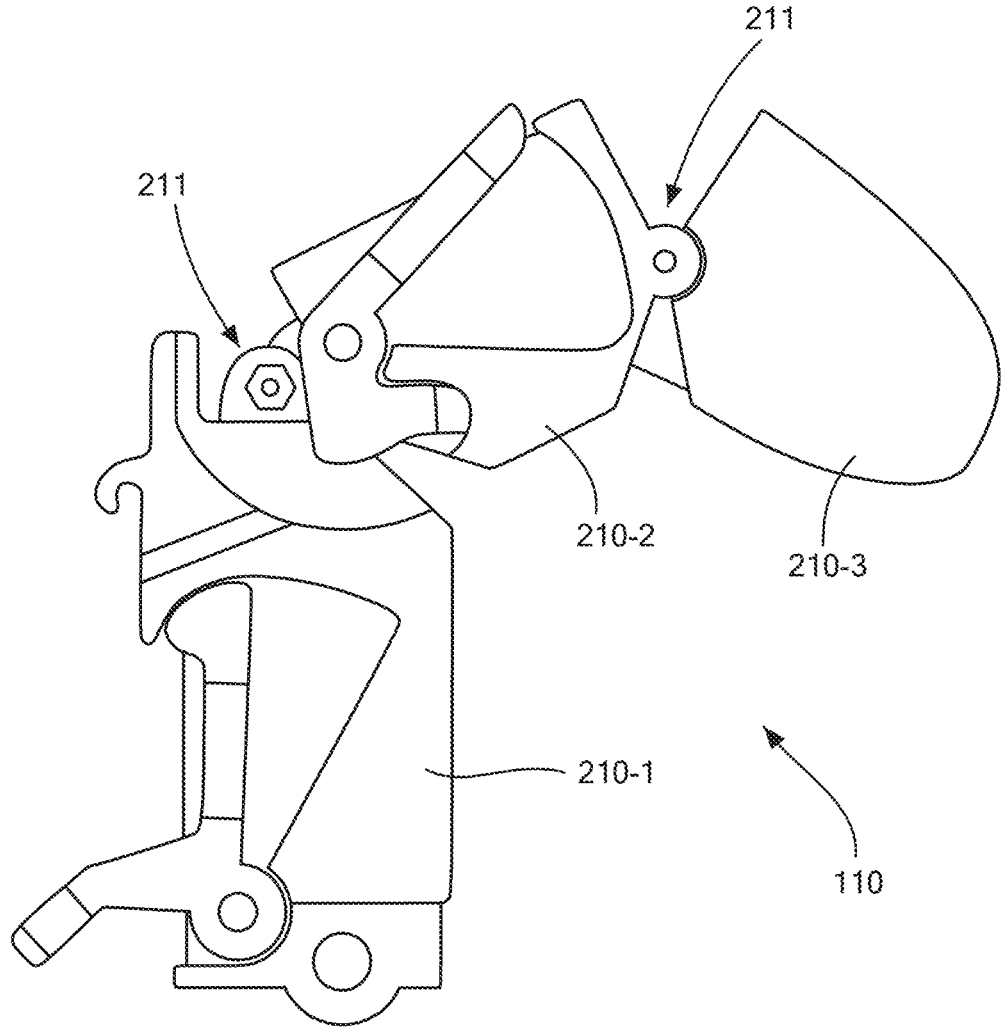

FIGS. 5A-5C show views of a full digit prosthetic in the prosthetic apparatus of FIGS. 1, 3A and 3B. Referring to FIGS. 4 and 5, the prosthetic member 110 includes articulated segments 210-1 . . . 210-3, each joined by a respective hinge 211.

FIGS. 6A-6G show control of the full digit prosthetic of FIGS. 5A-5C. Referring to FIGS. 1-6E, the full digit prosthetic 110 and corresponding control includes, for each articulated portion, a hinged, circumferential strap 130, 135 on an articulated portion of the functional digit, and a hinge forming a pivotal engagement with an adjacent circumferential strap. A two degree-of-freedom linkage between the prosthetic member 110 and the functional digit 132 provide that both the prosthetic member and the functional digit having corresponding articulated portions 210-N, 232-N. Both tethered and rigid extension member 152 control may be achieved. For the proximate, or metacarpal phalange, the rigid extension member 152 links from the proximate articulated portion 232-1 of an adjacent functional digit 132 to the corresponding articulated portion 210-1 of the prosthetic digit 110. Concurrently, a tethered 150 attachment from a more distal articulated portion 232-2 of the adjacent functional digit runs to the corresponding articulated portion 210-2 of the prosthetic member 110.

Figure 6A:
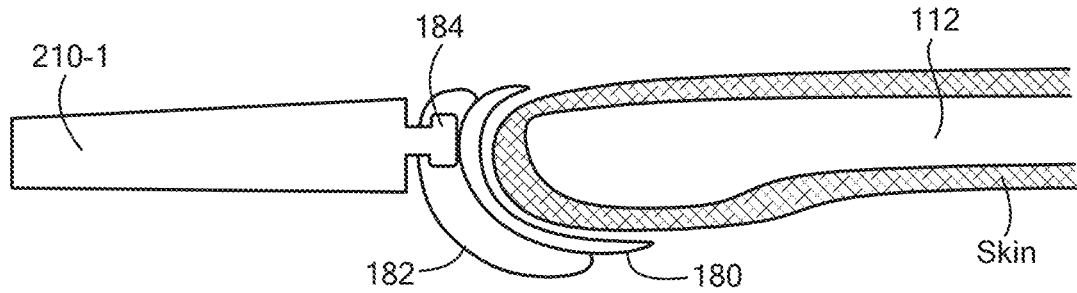
FIGS. 6A-6G show control of the full digit prosthetic of FIGS. 5A-5C.
Figure 6B:
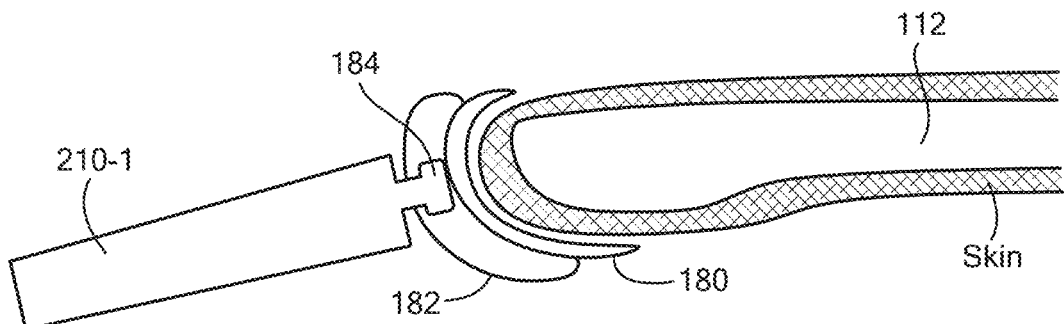
Figure 6C:
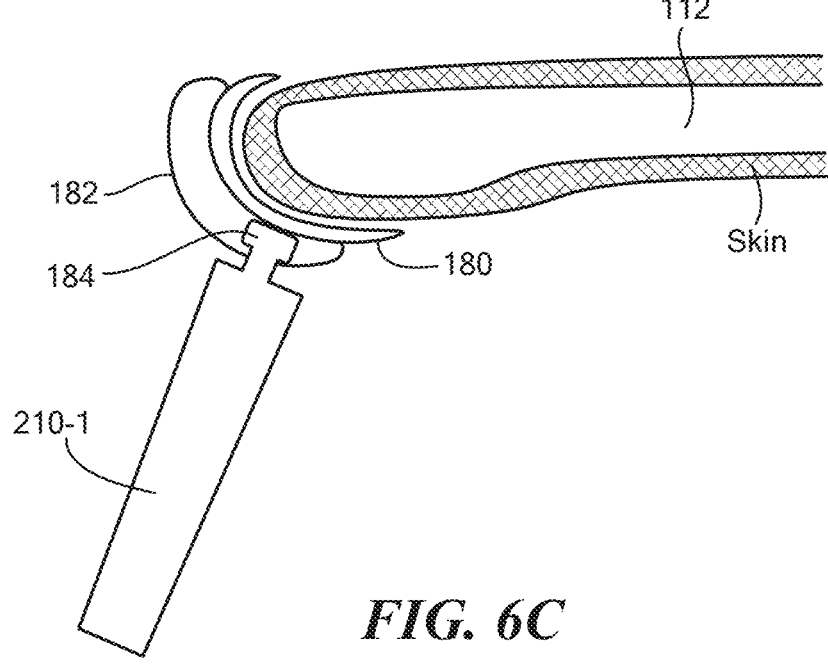
Figure 6D:
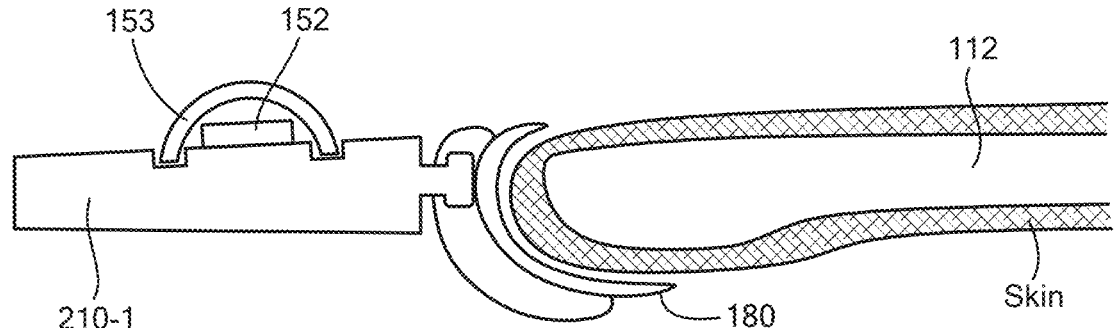
Figure 6E:
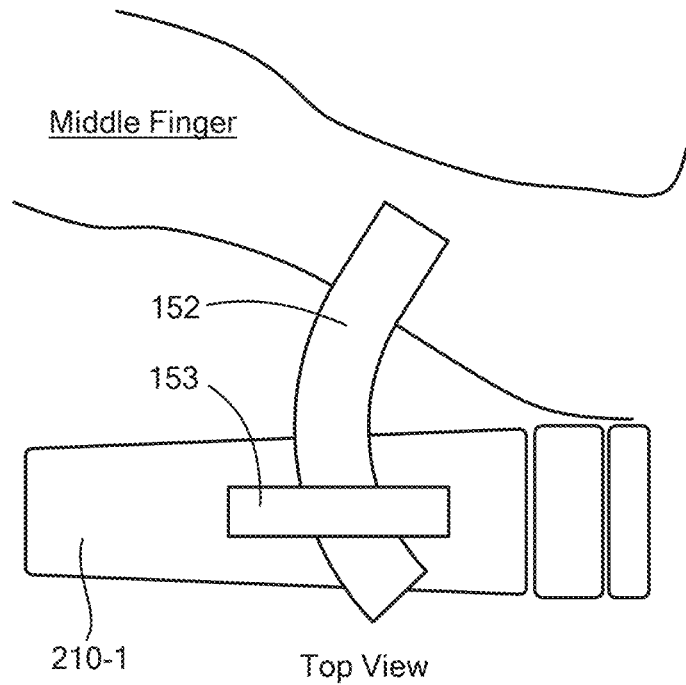

FIGS. 6A-C show articulation of the proximal articulated segment 210-1. A bone void 112 is defined by the existing wrist 145. A rubbery or resilient interface 180 cushions the attachment, while a slot 182 is slidably engaged by a tab 184 on the first articulated segment 210-1 for movement as shown by arrows from FIGS. 6A-6C. FIG. 6D shows a side view of the extension member 152 secured by band 153 for slidable lateral tolerance. FIG. 6E shows movement imparted from the adjacent functional digit 132, an index finger in the example shown.

Figures 6F, 6G:
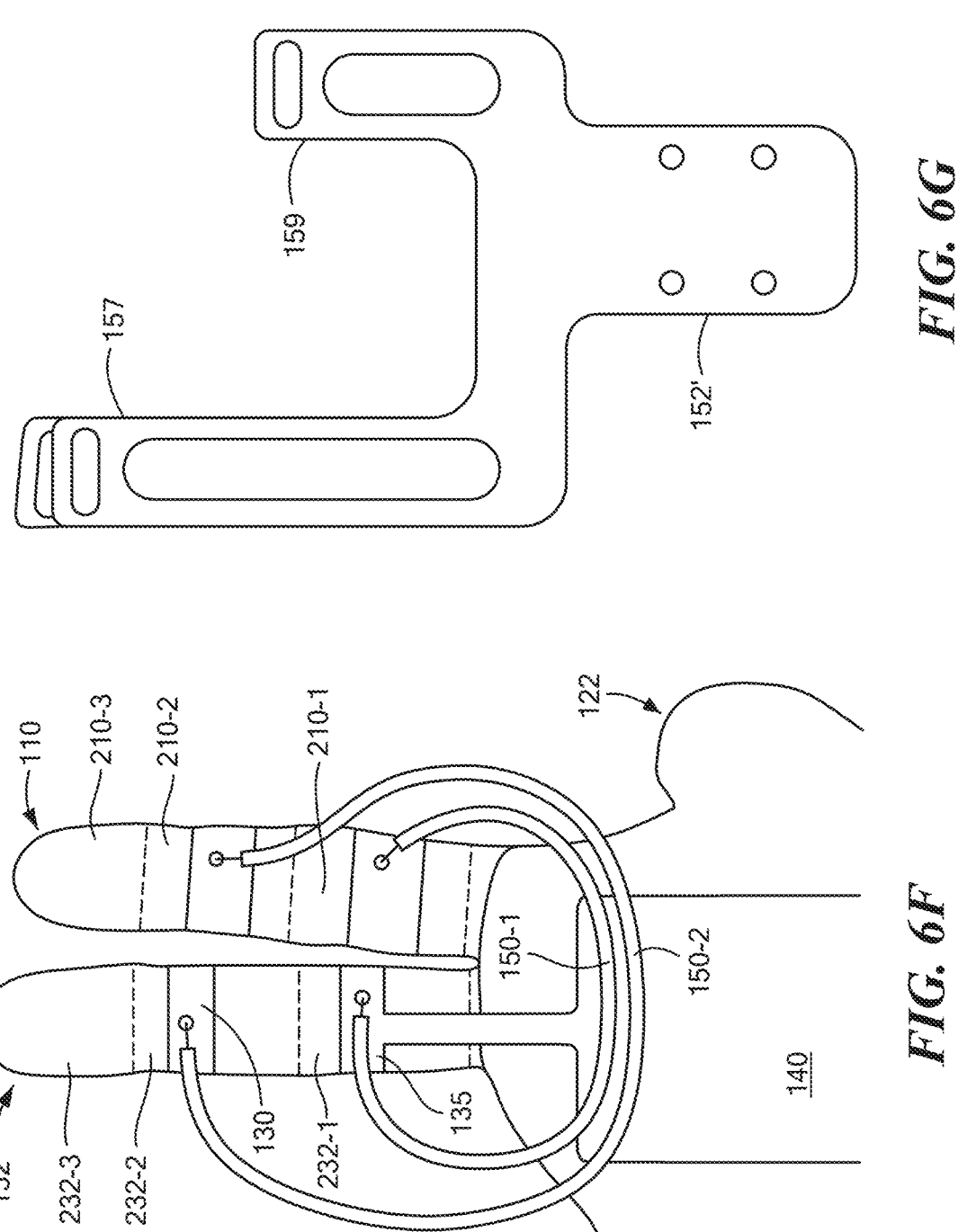

An alternate tethered control for any of the phalanges is shown in FIG. 6F. In FIG. 6F, a plurality of tethered attachments 150-N run between the prosthetic member 110 and the functional digit 132, such that each tethered attachment is between respective articulated portions 232-N, 110-N of the prosthetic member and the functional digit, thereby providing at least 2 degrees of freedom of movement of the prosthetic member. A single cable 150 between corresponding articulated segments imposes a Bowden cable for bidirectional use. Multiple tensioned cables may provide equivalent bidirectional operation. A particular configuration employs the extension member 152 for control of the proximate portion 110-1 with tethers to the more distal 110-2 portion. FIG. 6G shows an enhanced version of the extension member 152' for gaining additional leverage from a middle finger wing 157 and an index finger wing 159.

Figures 8A, 8B, 8C:
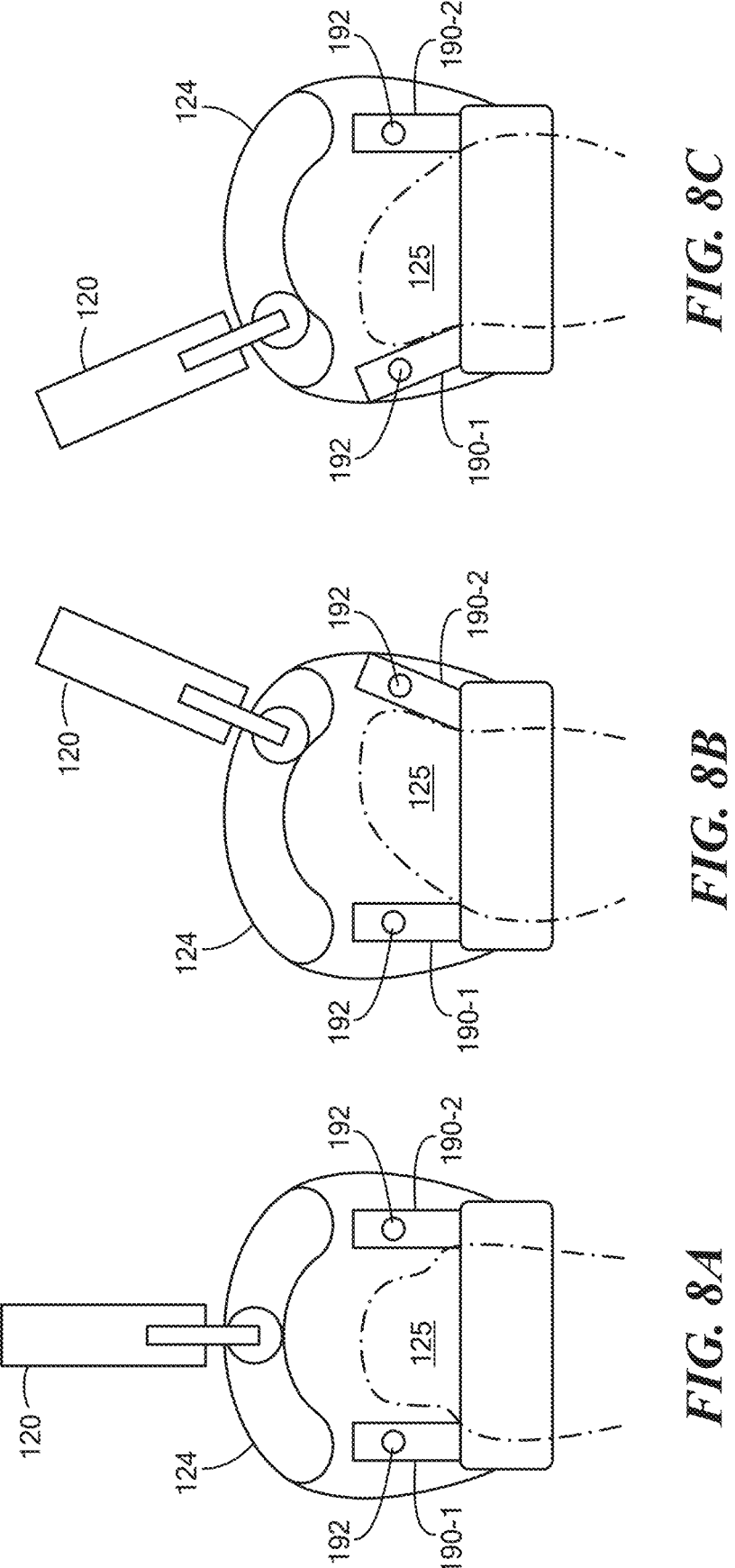
FIGS. 8A-8C show control of the partial digit prosthetic of FIGS. 7A-7B.

FIGS. 7A-7B show views of a partial digit prosthetic apparatus of FIGS. 1, 3A and 3B. The partial digit prosthetic member 120 has a receptacle 124 for receiving and detecting movement of the residual metacarpal portion 125. FIGS. 8A-8C show control of the partial digit prosthetic of FIGS. 7A-7B. Referring to FIGS. 7A-8C, the metacarpal portion 125 has sufficient range of movement in the receptacle 124 to depress or contact sensors 190-1 . . . 190-2 (190 generally) as the metacarpal portion 125 moves between 125-R and 125-L. Sensors 190 impart a control signal to the actuator 160 for movement of the prosthetic member 120.

The sensors 190 may further comprise variable electric substance, such that the variable electric substance is configured to render an altered resistance in response to compression from the metacarpal portion 125. Actuator logic responsive to the voltage level interprets the voltage drop or increase as activation of a respective sensor 190, and disposes the prosthetic member 120 based on the altered resistance.

The variable electric substance may include a flexible tube 192, where a conductive liquid is encapsulated in the flexible tube, such that the liquid has varied electrical properties in response to contact from the metacarpal portion.

Figure 9:
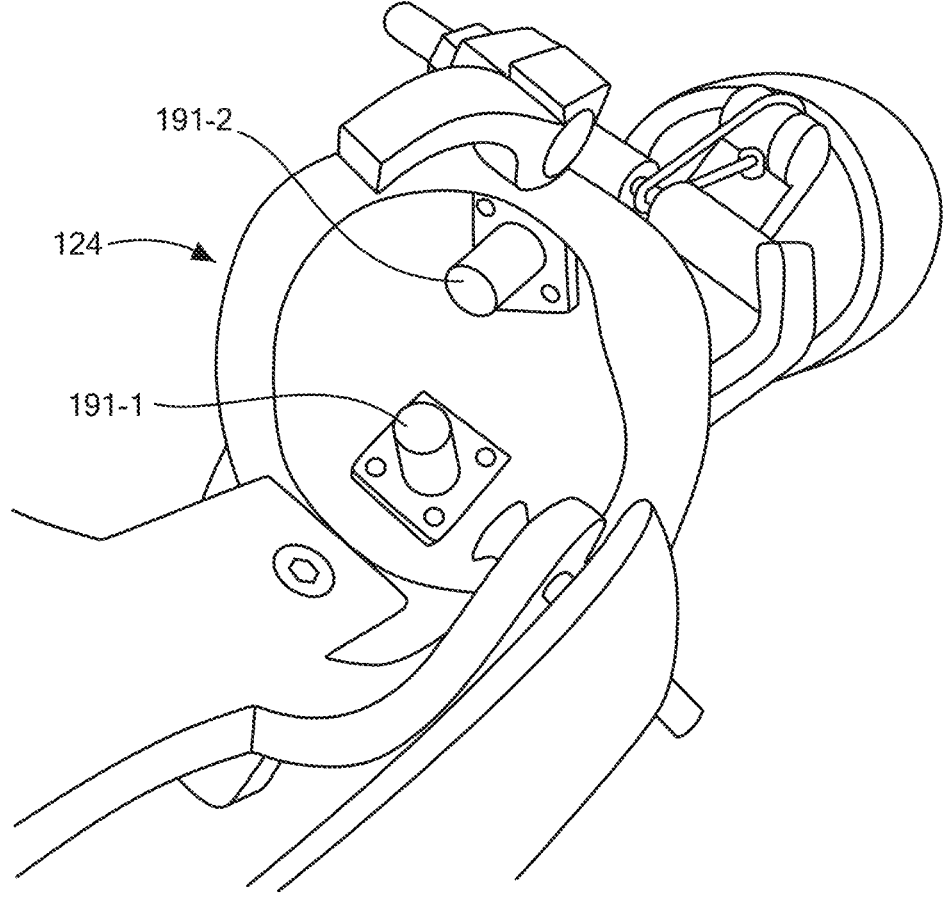
FIG. 9 shows an alternate control approach for the partial digit prosthetic of FIGS. 7A-7B.

A further variation is shown in FIG. 9, where opposed contact elements 191-1 . . . 191-2 (191 generally) define the sensor. Each contact element 191 of the opposed contact elements detects movement resulting from a depression from the metacarpal portion. The contact elements 191 are in turn connected to the actuator 160 for disposing the prosthetic member 120 in a direction opposite from the other opposed contact element. Two contact elements 191 are shown, corresponding to articulated contraction and extension of the prosthetic member, however additional inputs and/or voltage thresholds may be established.

Figure 10A:
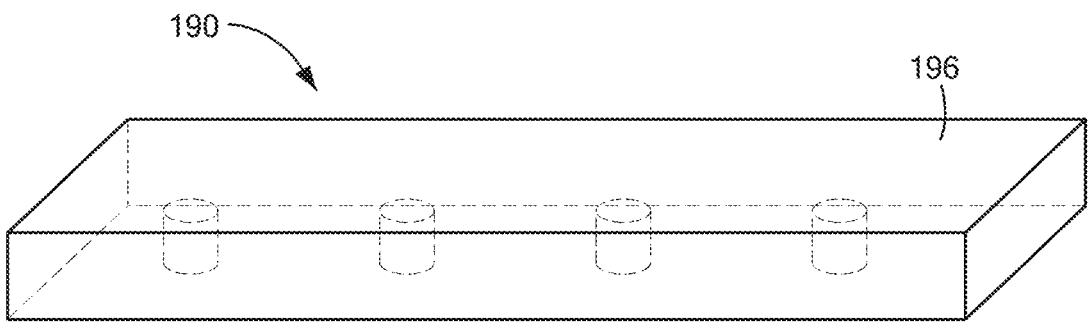
FIGS. 10A-10C show a magnetic based control approach the partial digit prosthetic of FIGS. 7A-7B.
Figure 10B:
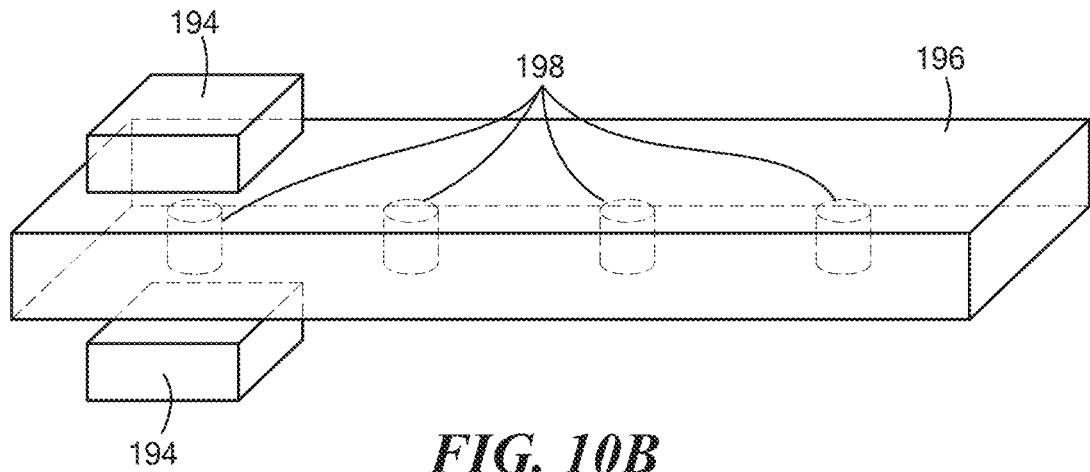
Figure 10C:
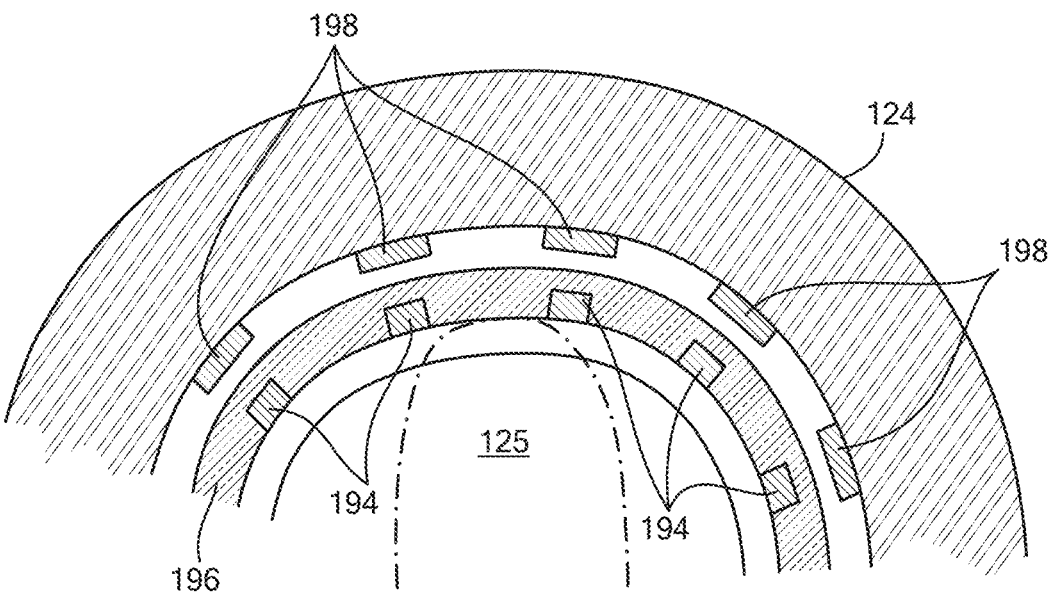

For example, FIGS. 10A-10C show a magnetic based control approach of the partial digit prosthetic of FIGS. 7A-7B. Referring to FIGS. 7A-10C, an array of magnetic sensing elements 198 surrounds an interior of the receptacle 124. A deformable, moldable substrate 196 such as silicon defines the sensor 190. A complementary array of aligned Hall effect (magnetic) sensors 198 are disposed on the interior of the receptacle 124. The substrate 196 has recesses for receiving magnets 194 at various positions. As the metacarpal portion 125 moves, an interference engagement occurs between the resilient band and the metacarpal portion, which disposes the magnetic elements 194 towards the magnetic sensors based on a deformation of the resilient substrate band. The metacarpal portion 125 compresses the deformable substrate 196 to dispose an aligned magnet 194 closer to the corresponding magnetic sensing element 198, identifying the position of the metacarpal portion 125 based on which Hall effect sensor was triggered.

Figures 11A, 11B:
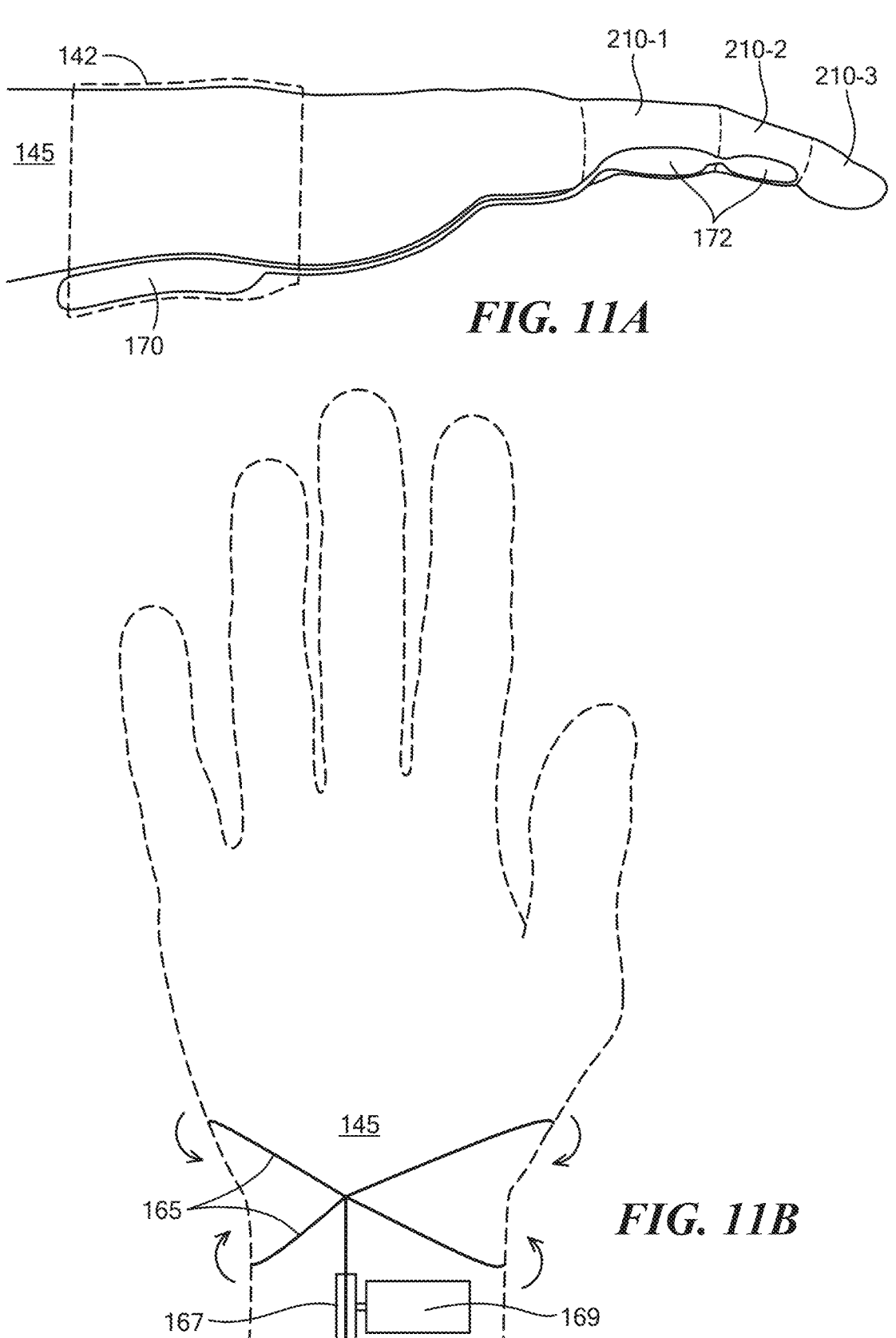
FIGS. 11A-11B show alternate configurations of the variable compression harness for securing the prosthetic apparatus of FIGS. 1, 3A and 3B.

FIGS. 11A-11B show a tether based variable compression harness for securing the prosthetic apparatus of FIGS. 1, 3A and 3B. Referring to FIGS. 11A-11B, the variable restraint discussed above disposes a fluid repository 170 and bladder 172 between the wrist 145 and housing 140 to more securely engage the prosthetic apparatus 100 to the wrist 145. An alternate arrangement provides a tethered arrangement where wraparound tethers 165 engage the wrist 145 and harness 142, tightened in common by a pully 167 and actuator 169 for winding the tethers 165 tighter.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. For a partial amputation of a digit, a prosthetic device adapted to engage a post amputation metacarpal portion having residual movement, comprising:
 a prosthetic member having a base defining a receptacle adapted to engage the metacarpal portion;
 a sensor on the base responsive to movement of the metacarpal portion; and
 an actuator responsive to the sensor for disposing the prosthetic member responsive to the sensor,
 wherein the sensor further comprises a variable electric substance, the variable electric substance configured to render an altered resistance in response to compression from the metacarpal portion, further comprising actuator logic for disposing the prosthetic member based on the altered resistance.

2. The device of claim 1 further comprising opposed contact elements defining the sensor, each contact element of the opposed contact elements detecting movement resulting from a depression from the metacarpal portion, each contact element connected to the actuator for disposing the prosthetic member in a direction opposite from the other opposed contact element.

3. The device of claim 1 further comprising a motor driven pulley, the motor driven pulley operable to retract a tether attached to the prosthetic member in response to the altered resistance.

4. The device of claim 1 further comprising a locking solenoid, the locking solenoid responsive to stoppage of the motor driven pulley for maintaining a position of the tether and attached prosthetic member under a load.

5. The device of claim 1 wherein the sensor further comprises:
 a flexible tube; and
 a conductive liquid encapsulated in the flexible tube, the liquid having varied electrical properties in response to contact from the metacarpal portion.

6. The device of claim 1 wherein the base further comprises:
 a wrist harness configured to engage a wrist, the metacarpal portion extending from the wrist harness;
 a receptacle on the flexible substrate for receiving the metacarpal portion; and
 a fluid bladder disposed between a flexible substrate and the wrist, the fluid bladder extending to the prosthetic member and responsive to compression of the prosthetic member for forcing fluid between the wrist and the flexible substrate.

7. The device of claim 1 further comprising:
 a fluid receptacle attached to a wrist harness, the wrist harness supporting the prosthetic member;
 a bladder extending along the prosthetic member and coupled to the fluid receptacle for forming a closed fluid volume,
 the bladder formed from a flexible material and disposed to compress based on a gripping force exerted by the prosthetic member, the compression forcing fluid into the fluid receptacle for compressing the wrist harness against the fluid receptacle.

8. A prosthetic device, comprising:
 a first prosthetic member adapted to engage a digit void resulting from a complete amputation;

a second prosthetic member adapted to engage a partially
amputated digit portion;

a respective actuator engaged with each respective first
and second prosthetic members, the respective actuators including:

a tethered attachment configured to engage an adjacent
functional digit, the first prosthetic member responsive to the tethered attachment for movement of the
first prosthetic member; and a sensor responsive to movement of the digit portion,
the sensor connected to a powered actuator for
moving the second prosthetic member.

\* \* \* \* \*